United States Patent

Szente

[11] 4,031,078
[45] June 21, 1977

[54] BENZODIAZEPINE DERIVATIVES

[75] Inventor: Andre Szente, Basel, Switzerland

[73] Assignee: Hoffmann-La Roche Inc., Nutley, N.J.

[22] Filed: Oct. 14, 1975

[21] Appl. No.: 622,291

[30] Foreign Application Priority Data
Oct. 21, 1974 Switzerland .............................. 14049/74

[52] U.S. Cl. ......................... 260/239.3 D; 424/244
[51] Int. Cl.² ........................................ C07D 243/22
[58] Field of Search ............................ 260/239.3 D

[56] References Cited
UNITED STATES PATENTS

| | | | |
|---|---|---|---|
| 3,121,076 | 2/1964 | Keller et al. | 260/239.3 D |
| 3,422,091 | 1/1969 | Archer et al. | 260/239.3 D |

OTHER PUBLICATIONS

Sunjic et al., "J. Het. Chem." vol. 10, Aug. 1973, pp. 591–599.
Sternbach et al., "Some Aspects of Structure–Activity Relationship in Psychotropic Agents of the 1,4-Benzodiazepine Series" A symposium held at the Regional Research Laboratory, Hyderbad, India CS1R New Delhi, India, 1966.

Primary Examiner—Henry R. Jiles
Assistant Examiner—Robert T. Bond
Attorney, Agent, or Firm—Samuel L. Welt; Bernard S. Leon; Frank P. Hoffman

[57] ABSTRACT

This invention is directed toward pharmacologically active compounds of the formula

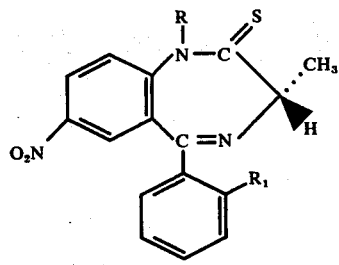

wherein R represents a hydrogen atom or a lower alkyl group and $R_1$ represents a hydrogen or halogen atom or a trifluoromethyl group which have the absolute configuration S at the 3-position carbon atom.

Also presented is a process to produce the above benzodiazepine derivatives and pharmaceutical preparations therefor. The above benzodiazepine derivatives exhibit pronounced anthelmintic, especially schistosomicidal, activity and muscle relaxant, anticonvulsant and sedative activities.

4 Claims, No Drawings

BENZODIAZEPINE DERIVATIVES

The present invention relates to benzodiazepine derivatives. More particularly, the invention is concerned with benzodiazepine derivatives, a process for the manufacture thereof and pharmaceutical preparations containing same.

The benzodiazepine derivatives provided by the present invention are optically active 1,4-benzodiazepin-2-thiones of the general formula

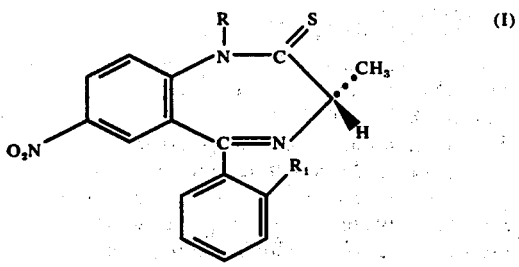

wherein R represents a hydrogen atom or a lower alkyl group and $R_1$ represents a hydrogen or halogen atom or the trifluoromethyl group, which have the absolute configuration S at the carbon atom in the 3-position.

As used in this specification, the term "lower alkyl" denotes a straight-chain or branched-chain hydrocarbon group containing a maximum of 6 carbon atoms such as the methyl, ethyl, propyl, isopropyl, butyl groups and the like. The term "halogen" denotes chlorine, bromine, iodine and fluorine.

In a preferred embodiment of the present invention R1 represents a halogen atom, especially a chlorine or fluorine atom. When R represents a lower alkyl group, the methyl group is preferred.

As will be evident from the foregoing, especially preferred optically active 1,4-benzodiazepin-2-thiones of formula I are those in which $R_1$ represents a chlorine or fluorine atom and R represents a hydrogen atom or the methyl group.

A particularly preferred optically active 1,4-benzodiazepin-2-thione of formula I is (+)-5-(o-chlorophenyl)-1,3-dihydro-3-methyl-7-nitro-2H-1,4-benzodiazepin-2-thione.

According to the process provided by the present invention, the optically active 1,4-benzodiazepin-2-thiones of formula I hereinbefore are manufactured by treating a lactam of the general formula

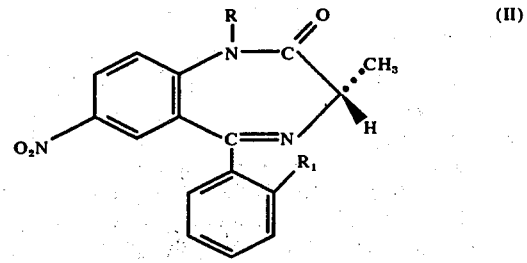

wherein R and $R_1$ have the significance given earlier, with a sulfuring agent.

The treatment of a lactam of formula II with a sulfuring agent is carried out in a manner known per se. According to a preferred procedure, a lactam of formula II can be treated with a sulfuring agent such as phosphorus pentasulfide.

In the aforementioned treatment, the sulfuring agent is preferably used in excess. The treatment is advantageously carried out in an inert organic solvent such as dioxane, methylene chloride or the like in the presence of triethylamine at a temperature of about 50° C to the reflux temperature of the mixture, preferably at the reflux temperature. Dioxane is a preferred solvent for this treatment.

The lactam starting materials of formula II are known compounds or can readily be prepared in a manner analogous to the known compounds.

In carrying out the process provided by the present invention, the conditions are always chosen so that substantially no racemisation can occur.

The optically active 1,4-benzodiazepin-2-thiones of formula I are useful as medicaments. They possess an extremely pronounced anthelmintic, especially schistosomicidal, activity and, in addition, exhibit the muscle relaxant, anticonvulsant and sedative activity which is common in benzodiazepines. Surprisingly, it has been shown that the corresponding antipodes having the absolute configuration R as well as the corresponding racemates exhibit no anthelmintic activity and respectively only slight anthelmintic activity. The optically active 1,4-benzodiazepin-2-thiones of formula I can be used, for example, for the therapy of bilharzia. The following test is given by way of example to demonstrate the schistosomicidal activity of the optically active 1,4-benzodiazepin-2-thiones of formula I.

Mice are infected subcutaneously with 60 cercaria of Schistosoma mansoni. Approximately 42 days after the infection, the mice are treated with the substances to be tested on 5 successive days. 5–10 mice are used per substance and dosage (mg/kg). 10 untreated mice are used as controls. The section is carried out 6 days or 2–3 weeks after termination of the treatment. Worm pairs in the mesenteric veins, portal vein and liver are dissected out and counted. The percentage distribution of the worm pairs in the mesenteric veins, portal vein and liver is calculated and the condition of the worms (living, dead) registered. The activity of the test substance is shown in an increased proportion of the worms in the vessels of the lier and in the appearance of dead worms.

For evaluation, the percentage proportion of living and dead worm pairs in the vessels of the liver is compared not only in the infected treated mice but also in the infected, but untreated, control mice. The determination of the $SD_{50}$ (Shift Dose 50%: dose which dispels 50% of the worm pairs into the liver in a group of treated mice) and $VD_{50}$ (Vermicidal Dose 50%: dose which kills 50% of the worm pairs) is carried out according to the probit analysis.

Two test results are compiled in the following Table:

Table

| Test substance | $SD_{50}$ mg/kg | $VD_{50}$ mg/kg |
| --- | --- | --- |
| (+)-5-(o-chlorophenyl)-1,3-dihydro-3-methyl-7-nitro-2H-1,4-benzodiazepin-2-thione | 78 | 135 |

The optically active 1,4-benzodiazepin-2-thiones of formula I can be used as medicaments, for example, in the form of pharmaceutical preparations which contain them in association with a compatible pharmaceutical carrier. This carrier can be an organic or inorganic carrier material suitable for enteral or parenteral administration such as gelatine, lactose, starch, gum arabic, magnesium stearate, talcum, vegetable oils, polyalkyleneglycols, petroleum jelly and the like. The pharmaceutical preparations can be made up in a solid form (e.g. as tablets or dragees) or in a liquid form (e.g. as solutions, suspensions or emulsions). They can contain adjuvants such as preservatives, stabilisers, wetting agents, emulsifiers, salts for varying the osmotic pressure or buffers. The pharmaceutical preparations can contain additional therapeutically active substances.

Expedient pharmaceutical dosage forms contain 5–50 mg, preferably about 5 mg, of an optically active 1,4-benzodiazepin-2-thione of formula I.

The dosage is selected according to the individual requirements. For example, the present optically active 1,4-benzodiazepin-2-thiones can be administered in dosages of from about 0.1 mg/kg to about 10 mg/kg per day p.o., preferably 0.3 mg/kg per day p.o. This amount can be administered in a single dosage or in several subdivided dosages according to the needs of the patient and the instructions of the attending physician. This dosage is expediently administered, having regard to the condition of the patient, on several successive days, preferably on 5 to 8 successive days.

The following Examples illustrate the present invention:

EXAMPLE 1

2.6 g of (+)-5-(o-chlorophenyl)-1,3-dihydro-3-methyl-7-nitro-2H-1,4-benzodiazepin-2-one are dissolved in 40 ml of dioxane and treated with 1.6 g of phosphorus pentasulfide and 0.7 ml of triethylamine. The mixture is then heated to reflux for 20 minutes, cooled with ice and concentrated on a rotary evaporator. The residue is treated with 10% bicarbonate solution and ethyl acetate, and the ethyl acetate phase is washed twice with 10% bicarbonate solution, dried with sodium sulfate, filtered and concentrated. The residue is purified on a 60 g silica gel column using methylene chloride and methylene chloride/ethyl acetate (20:1) for the elution and then crystallised from methylene chloride/petroleum ether. There is obtained (+)-5-(o-chlorophenyl)-1,3-dihydro-3-methyl-7-nitro-2H-1,4-benzodiazepin-2-thione which melts at 258°–260° C and which exhibits a rotation of $[\alpha]_{25}^{D}=+160.6°$ (in methylene chloride, 1%).

The starting material can be prepared as follows:

82 g of carbobenzoxy-L-alanine are dissolved in 100 ml of absolute tetrahydrofuran, the solution is cooled to −40° C and treated with 80 g of phosphorus pentachloride. The mixture is stirred at −30° C for 20 minutes and subsequently added to a shaken solution of 80 g of 2-amino-5-nitro-2′-chlorobenzophenone in 100 ml of absolute tetrahydrofuran. The solution is concentrated on a rotary evaporator at 50°–60° C, treated twice with toluene and evaporated each time. By crystallisation of the residue from ether, there is obtained (−)-benzyl-[1-[ 2-(o-chlorobenzoyl)4-nitrophenylcarbamoyl]-ethyl]carbamate which melts at 147° C and exhibits a rotation of $[\alpha]_{25}^{D}=-18.2°$ (in methylene chloride, 1%).

9.2 g of the foregoing carbamate are stirred in 90 ml of a 30% solution of hydrogen bromide in glacial acetic acid for 2 hours at room temperature and then the mixture is concentrated on a rotary evaporator. The residue is dissolved in water, the aqueous solution washed three times with ether and then made alkaline with sodium bicarbonate. The precipitated product is extracted with methylene chloride, the methylene chloride phase dried over sodium sulfate and concentrated. The residue is crystallised from ether and recrystallised from methylene chloride/petroleum ether, there being obtained (+)-2-amino-2′-(o-chlorobenzoyl)4′-nitropropiononailide which melts at 132° C and exhibits a rotation of $[\alpha]_{25}^{D}=+4.4°$ (in methylene chloride, 2%).

35 g of the foregoing propionoanilide are heated to reflux in 40 ml of glacial acetic acid and 200 ml of absolute toluene for 15 minutes. The residue obtained after distillation of the solvent is treated with methylene chloride and 10% sodium bicarbonate solution. The methylene chloride solution is washed twice with 10% sodium bicarbonate solution and once with water, dried over sodium sulfate, filtered and concentrated. The residue is taken up in benzene, some racemate formed crystallising out and being filtered off. The benzene solution is evaporated and the residue crystallised from ether to give (+)-5-(o-chlorophenyl)-1,3-dihydro-3-methyl-7-nitro-2H-1,4-benzodiazepin-2-one which melts at 198°–200° C and exhibits a rotation of $[\alpha]_{25}^{D}=+252.1°$ (in methylene chloride, 1%).

EXAMPLE 2

32 g of (+)-5-(o-fluorophenyl)-1,3-dihydro-3-methyl-7-nitro-2H-1,4-benzodiazepin-2-one are dissolved in 450 ml of absolute dioxane and treated with 21 g of phosphorus pentasulfide and 15 ml of triethylamine. The mixture is heated to reflux for 20 minutes, cooled with ice and concentrated on a rotary evaporator. The residue is treated with 10% bicarbonate solution and ethyl acetate and the ethyl acetate phase is washed twice with 10% bicarbonate solution, dried with sodium sulfate, filtered and concentrated. Crystallisation of the residue from ethanol yields racemate. By concentration of the mother liquor, there is obtained crude (+)-5-(o-fluorophenyl)-1,3-dihydro-3-methyl-7-nitro-2H-1,4-benzodiazepin-2-thione which exhibits a rotation of $[\alpha]_{25}^{D}=+319.1°$ (in methylene chloride, 1%).

The starting material can be prepared as follows:

90 g of carbobenzoxy-L-alanine are dissolved in 500 ml of absolute methylene chloride, the solution is cooled to −40° C and treated with 95 g of phosphorus pentachloride. The mixture is stirred at −30° C for 20 minutes and subsequently added to a shaken solution of 52 g of 2-amino-5-nitro-2′-fluorobenzophenone in 250 ml of absolute methylene chloride. The solution is concentrated on a rotary evaporator at 50°–60° C, treated twice with toluene and evaporated each time. By crystallisation of the residue from ether, there is obtained (−)-benzyl-[1-[ 2-(o-fluorobenzoyl)-4-nitrophenyl -carbamoyl]ethyl]carbamate which melts at 158°–160° C and exhibits a rotation of $[\alpha]_{25}^{D}=-23.4°$ (in methylene chloride, 1%).

35 g of the foregoing carbamate in 50 ml of methylene chloride and 110 ml of a 30% solution of hydrogen bromide in glacial acetic acid are stirred for 20 minutes at room temperature and then the mixture is concentrated on a rotary evaporator. The residue is dissolved in water, the aqueous solution washed three times with ether, made alkaline with sodium bicarbonate and extracted three times with ethyl acetate. The combined ethyl acetate extracts are dried over sodium sulfate and concentrated.

The crude product obtained according to the preceding paragraph is heated to reflux in 30 ml of glacial acetic acid and 220 ml of absolute toluene for 20 minutes. The residue obtained after distillation of the solvent is treated with methylene chloride and 10% sodium bicarbonate solution. The methylene chloride solution is washed twice with 10% sodium bicarbonate solution and once with water, dried over sodium sulfate, filtered and concentrated. Fractional crystallisation of the residue, first from benzene and then from ether/petroleum ether, yields (+)-5-(o-fluorophenyl)-1,3-dihydro-3-methyl-7-nitro-2H-1,4-benzodiazepin-2-one which melts at 130°–140° C and exhibits a rotation of $[\alpha]_{25}^{D} = +358.1°$ (in methylene chloride, 1%).

The following Examples illustrate typical pharmaceutical preparations containing the optically active 1,4-benzodiazepin-2-thiones of formula I as the active ingredient:

Example A

Tablets of the following composition are manufactured:

| | |
|---|---|
| Active ingredient of formula I | 5.0 mg |
| Lactose | 100.0 mg |
| Maize starch | 85.0 mg |
| Ethylcellulose | 10.0 mg |
| Talcum | 4.5 mg |
| Magnesium stearate | 0.5 mg |
| | 205.0 mg |

The active ingredient is mixed with the lactose and the maize starch and granulated with a solution of the ethylcellulose in 40 ml of methylene chloride. The granulate is dried at 40° C, mixed with the talcum and magnesium stearate and pressed to tablets.

| | |
|---|---|
| Weight of one tablet | 205 mg |
| Active ingredient content of one tablet | 5 mg |

EXAMPLE B

Capsules containing the following ingredients are manufactured:

| | |
|---|---|
| Active ingredient of formula I | 5.0 mg |
| Lactose | 155.0 mg |
| Maize starch | 30.0 mg |
| Talcum | 15.0 mg |
| | 205.0 mg |

The active ingredient is homogeneously mixed with the lactose and the maize starch, passed through a sieving machine and, after intermixing of the talcum, filled into gelatine capsules.

| | |
|---|---|
| Fill-weight of capsule | 205 mg |
| Active ingredient content | 5 mg |

What is claimed:

1. A compound of the formula

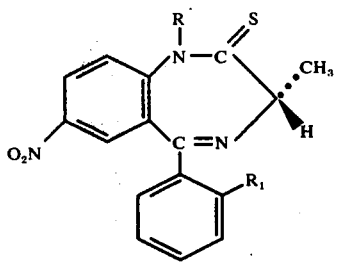

wherein R represents a hydrogen atom or a lower alkyl group and $R_1$ represents a hydrogen or halogen atom or a trifluoromethyl group,
which has the absolute configuration S at the carbon atom in the 3-position.

2. The compound of claim 1 wherein R represents a hydrogen atom or a methyl group and $R_1$ represents a chlorine or fluorine atom.

3. A compound of the formula: (+)-5-(o-chlorophenyl)-1,3-dihydro-3-methyl-7-nitro-2H-1,4-benzodiazepine-2-thione.

4. A compound of the formula: (+)-5-(o-fluorophenyl)-1,3-dihydro-3-methyl-7-nitro-2H-1,4-benzodiazepine-2-thione.

* * * * *